United States Patent [19]

Warden et al.

[11] 3,951,387
[45] Apr. 20, 1976

[54] CARTRIDGE FOR STORING AND MIXING AT LEAST TWO INDEPENDENT INGREDIENTS

[75] Inventors: Fuller Warden; Eugene W. Lewis, both of Tulsa, Okla.

[73] Assignee: Grace Development Company, Tulsa, Okla.

[22] Filed: Apr. 25, 1975

[21] Appl. No.: 571,523

[52] U.S. Cl.................................. 259/67; 206/219; 259/122; 259/DIG. 20
[51] Int. Cl.² .......................................... B01F 7/24
[58] Field of Search ............. 259/107, 108, 64, 65, 259/66, 67, 118, 119, 120, 121, 122, DIG. 20; 206/219, 220

[56] References Cited
UNITED STATES PATENTS

| | | | |
|---|---|---|---|
| 3,326,531 | 6/1967 | Matheson | 259/67 |
| 3,342,460 | 9/1967 | Bolde | 259/122 |
| 3,640,510 | 2/1972 | Lea | 259/122 |
| 3,679,184 | 7/1972 | Woodham | 259/DIG. 20 |
| 3,809,225 | 5/1974 | Pierre | 206/220 |

*Primary Examiner*—Robert W. Jenkins
*Attorney, Agent, or Firm*—Mildred K. Flowers

[57] ABSTRACT

A disposable cartridge or capsule for storing at least two independent ingredients preloaded therein in mutually sealed relationship, and selectively combining and mixing the ingredients to provide a substantially homogeneous compound. The cartridge comprises a sectional housing having mixer means rotatably mounted therein, said mixer means being carried by sealing means which cooperates with the housing for providing at least two sealed compartments therein in one position of the sealing means and opening communication between the compartments in a second position of the sealing means. Subsequent to a mixing operation, one of said housing sections may be separated from the other housing section and released from engagement with the sealing means and mixing means whereby the mixture may be stored in said removed housing section for use.

9 Claims, 2 Drawing Figures

CARTRIDGE FOR STORING AND MIXING AT LEAST TWO INDEPENDENT INGREDIENTS

CROSS-REFERENCE TO RELATED APPLICATION

This application is related to our co-pending application Ser. No. 508,256, filed Sept. 23, 1974, and entitled "Combined Amalgam Carrier and Dental Handpiece".

BACKGROUND OF THE INVENTION

1. Field of the Invention

This invention relates to improvements in packaging and mixing apparatus and more particularly, but not by way of limitation, to a disposable cartridge or capsule for storing at least two independent ingredients preloaded therein in mutually sealed relationship and having means for selectively combining the ingredients.

2. Description of the Prior Art

The usual method in widespread use today for filling a tooth cavity with amalgam, or the like, comprises placing a preselected quantity of silver and mercury in a suitable vessel or container for mixing thereof to produce the amalgam. These containers frequently comprise housings having at least two internal compartments therein sealed from one another, and each compartment being provided with one of the ingredients of the amalgam. A pestle is normally disposed within one of the housings, and when the two ingredients are to be mixed to produce amalgam, the compartments are placed in communication with each other, and the housing or capsule is placed in a vibrator, or the like, whereby the pestle facilitates mixing of the silver and mercury within the capsule housing to produce the amalgam. A carrier tool is then filled with a charge of the amalgam and hand carried to the cavity for depositing the amalgam therein. Subsequent to placing a charge of amalgam in the tooth cavity, a second hand tool, commonly known as a plugger, is utilized for compacting or packing the amalgam into the cavity. It is usually necessary to place a plurality of amalgam charges in a single cavity, with a plugging operation subsequent to the placing of each amalgam charge in the cavity. In the event the cavity is relatively large, it is frequently necessary to mix an additional supply of amalgam. Thus, the filling of a tooth cavity can become tedious and time consuming in that the mixing of the components of the amalgam, even though prepacked in a single capsule, is somewhat burdensome because the thorough and efficient mixing of the ingredients requires a considerable period of time in the vibrator.

SUMMARY OF THE INVENTION

The present invention comtemplates an amalgam carrier or capsule comprising a housing having separable housing sections. Sealing means is provided on one housing section and in one position thereof seals the interior of the capsule in at least two individual compartments whereby a predetermined quantity of silver may be preloaded in one of said compartments, and a predetermined quantity of mercury may be preloaded in a second of said compartments. In a second position of the sealing means, communication is established between the individual compartments whereby the silver and mercury are intermingled. Mixing means is carried by the sealing means, and is rotatable within the capsule for efficiently mixing silver and mercury to provide amalgam. Subsequent to the mixing operation, the housing sections may be separated whereby the sealing means and mixing means remain in engagement with one of said housing sections, and the amalgam is contained within the other of said housing sections. The amalgam may then be utilized in the usual manner for filling a tooth cavity.

DESCRIPTION OF THE PREFERRED EMBODIMENT

Figure 1:
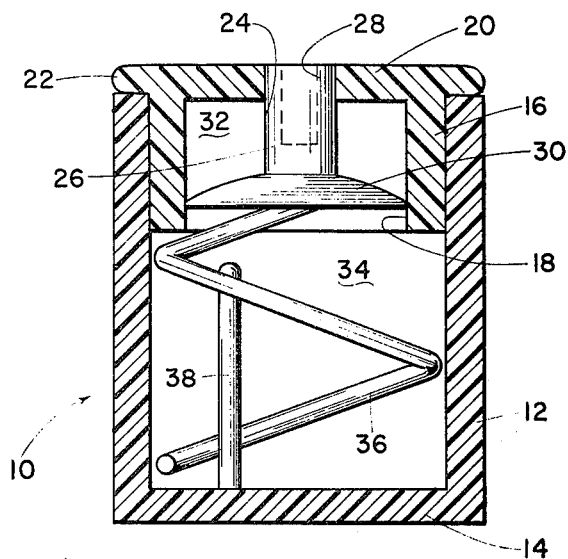
FIG. 1 is a sectional elevational view of a disposable capsule embodying the invention, with portions depicted in elevation, and illustrating one position thereof.

Referring to the drawings in detail, reference character 10 generally indicates a cartridge or capsule, which may be relatively small, particularly when used as an amalgam carrier, but not limited thereto. The capsule 10 comprises a first housing section 12 of a substantially cylindrical configuration, and preferably constructed from a suitable disposable plastic material. The housing section 12 is closed at one end by a wall 14 and is open at the opposite end thereof for slidably receiving a second housing member 16 therein. The housing 16 is also preferably constructed of a suitable disposable plastic material, and is open at one end 18 to provide communication with the interior of the housing 12, and is closed at the opposite end thereof by a wall 20. An outwardly extending circumferential flange 22 is provided around the outer periphery of the housing 16 for engagement with the open end of the housing 12 in order to limit the depth of insertion of the housing 16 within the housing 12, and to facilitate separation of the housing sections for a purpose and in a manner as will be hereinafter set forth.

A centrally disposed aperture 24 is provided in the wall 20 for receiving a rod or stem 26 therein. A central bore 28 is provided in the stem 26 and extends longitudinally therein for a purpose as will be hereinafter set forth. The cross-sectional configuration of the bore 28 is preferably provided with at least one flat side (not shown) or keyway (not shown), or the like, for a purpose as will be hereinafter set forth. A flange member or sealing means 30 is secured to or integral with the stem 26 and is of an outer diameterical size substantially equalt to the internal diameter of the housing 16 whereby the inner periphery of the housing 16 is sealingly engaged by the seal means 30 in one position of the rod 26 as particularly shown in FIG. 1. In this position for the seal means 30, the interior of the capsule 10 is separated into at least two individual sealed compartments 32 and 34.

Figure 2:
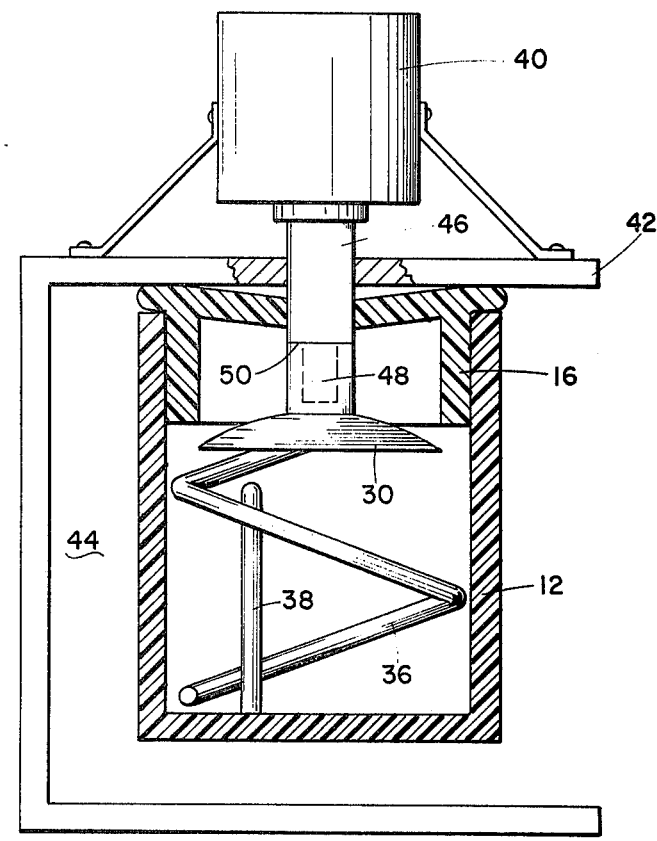
FIG. 2 is a sectional elevational view of a disposable capsule embodying the invention in connection with a power source, with portions depicted in elevation, and illustrating another position of the capsule.

A spiral mixer element 36 has one end thereof integral with or secured to the seal means 30 and the opposite end thereof freely disposed within the interior of the housing 12 when the housing sections 12 and 16 are in engagement as shown in FIGS. 1 and 2. It may be preferable to provide an offset, longitudinally extending post 38 in the interior of the housing 12 for facilitating the mixing operation, as will be hereinafter set forth. As shown herein, the post 38 is secured to or integral with the wall 14 and extends longitudinally inwardly within the housing 12, and is surrounded by the spiral mixing element 36. Of course, it is preferable that the stem 26, seal member 30, mixer element 36, and post 38 be constructed from a suitable disposable plastic material.

The capsule 10 is preferably preloaded with at least two ingredients, with one ingredient being preloaded into the chamber 32, and the other ingredient loaded into the chamber 34. Whereas the particular embodiment of the invention disclosed herein is particularly adapted for use with silver and mercury for producing amalgam for filling tooth cavities, it will be readily apparent that the apparatus may be utilized for housing and mixing substantially any ingredients which are to be maintained separated prior to the mixing thereof.

As shown herein, however, it is preferable to preload the chamber 32 with a preselected quantity of mercury and the chamber 34 with a preselected quantity of silver in any suitable or well known manner prior to assembly of the housing sections 12 and 16 to provide the capsule 10 with the most desirable ratio of silver and mercury for producing amalgam. The sealing engagement of the seal means 30 with the inner periphery of the housing 16 efficiently maintains the mercury sealed from contact with the silver, and the capsule may be utilized for storing the silver and mercury, which have been premeasured in preferred ratios for producing the desired end result for the amalgam.

When it is desired to produce amalgam for a tooth filling operation, or the like, the preloaded capsule 10 may be operably secured to a suitable power source, such as an electric motor 40, or the like, but not limited thereto. As shown in FIG. 2, the motor 40 is suitably mounted on a support plate or table 42 having a recess or cavity area 44 whereby the capsule 10 may be inserted within the cavity 44 and engaged with the drive shaft 46 of the motor 40. A longitudinally extending key or shaft element 48 is provided on the outer end of the drive shaft 46, and is of a reduced size to provide an annular shoulder 50. The cross sectional configuration of the shaft element 48 is complementary to the cross sectional configuration of the bore 28 for ready insertion therein. The engagement between the shaft element 48 and the bore 28 will transmit rotation to the stem 26 upon rotation of the drive shaft 46 due to the complementary key or flat surfaces (not shown) of the bore 28 and shaft 48.

When the capsule 10 is engaged with the shaft element 48, the outer end of the stem 26 will engage the shoulder 50, and a continued movement of the capsule 10 in the direction toward the motor 40, as viewed in FIG. 2, will cause the stem 26 to be displaced longitudinally and move into the interior of the housing 12. The bore 24 will then be in sealing engagement with the outer periphery of the drive shaft 46, and the sealing member 30 will be moved into the interior of the housing 12 to establish communication between the chambers 32 and 34, thus intermingling the ingredients within the housing 12. Of course, the movement of the capsule 10 in the direction toward the motor 40 will be limited by the engagement of the flange 22 with the under surface of the plate or table 42.

The complementary cross-sectional configuration of the shaft element 48 with respect to the bore 28 will transmit rotation to the stem 26 upon rotation of the drive shaft 46 due to the engagement of the complementary "flats" (not shown) provided on the shaft element 48 and in the bore 28, as is well known. The rotation of the stem 28 is transmitted to the spiral mixing element 36, and as the element 36 is rotated within the capsule housing 12, the silver and mercury are quickly and efficiently mixed to produce amalgam. It is to be noted that the outer diameter of the spiral element 36 is in substantially constant wiping engagement with the inner periphery of the housing 12 for assuring an efficient mixing operation, and the post 38 substantially precludes any build up of the ingredients in the interior of the spiral element during the mixing operation. Of course, in some instances, it may be desirable to eliminate the post 38.

Usually a relatively short period of agitation or rotation of the spiral mixing element 37 is required for an efficient mixing of the silver and mercury to produce the desired amalgam. When the ingredients have been properly mixed within the housing 12, the motor 40 may be deactivated, and the housing 12 may be manually withdrawn or separated from the housing 16. The stem 26, sealing means 30 and mixing element 36 remain in engagement with the housing 16, and only the housing 12 and amalgam contained therein will be removed. Normally, the slight amount of momentum still remaining in the mixing element 36 will be sufficient for casting or throwing all of the amalgam away from the element 36 and into the housing 12 as the housing 12 is removed. The housing 12 and amalgam contained therein may then be carried to the proper site for use of the amalgam in the usual manner.

Subsequent to use of the amalgam in the housing 12, the entire capsule 10, including the emptied housing 12, housing 16, stem 26, sealing means 30, and mixing element 36 may be discarded, and when a second amalgam quantity or charge is desired, another preloaded capsule 10 may be utilized in the manner as hereinbefore set forth for producing another amalgam charge.

From the foregoing, it will be apparent that the present invention provides a novel preloaded, disposable amalgam carrier and mixer wherein a quantity of ingredients in preselected ratios are stored therein in mutually sealed relationship until such time as it is desired to mix the ingredients. When the capsule is to be utilized as an amalgam carrier for dentistry purposes, preselected quantities of silver and mercury, in selected ratios, are preloaded into the capsule and maintained therein in sealed relationship with respect to one another. When amalgam is to be produced, the capsule may be quickly and easily manually engaged with a power source wherein the sealing means is initially released for intermingling of the silver and mercury, subsequent to which the mixing means is activated for thoroughly and efficiently mixing the silver and mercury for producing amalgam. When the mixing operation has been completed, the housing section containing the amalgam may be readily manually removed from engagement with the other housing section and associated elements whereby the amalgam may be utilized in the normal manner for filling tooth cavities.

Whereas the present invention has been described in particular relation to the drawings attached hereto, it should be understood that other and further modifications, apart from those shown or suggested herein may be made within the spirit and scope of this invention.

What is claimed is:

1. Cartridge means for storing and mixing at least two independent ingredients and comprising sectional housing means, sealing means carried by one of said housing means and disposed within the cartridge in one position for providing at least two independently sealed compartments therein and movable to a second position for providing communication between the compartments for intermingling of the ingredients, rotatable mixing means carried by the sealing means and extending into the interior of the housing for mixing the intermingled ingredients, and one of said housing sections being removable with respect to another of said housing sections and independent of the sealing means and mixing means for carrying the mixed ingredients to a site of use.

2. Cartridge means as set forth in claim 1 wherein the sectional housing and seal means and mixing means are constructed from a disposable material.

3. Cartridge means as set forth in claim 1 wherein longitudinally extending post means is provided in the interior of the sectional housing for cooperation with the mixing means for facilitating the mixing of the ingredients.

4. Cartridge means as set forth in claim 1 wherein one of the ingredients is silver and one of the ingredients is mercury, and the mixture of the ingredients is amalgam.

5. Cartridge means as set forth in claim 1 wherein the mixing means comprises a spiral element having one end secured to the seal means and the opposite end thereof freely disposed within the sectional housing.

6. Cartridge means as set forth in claim 5 wherein the outer periphery of the spiral element is in substantially constant wiping engagement with the inner periphery of the sectional housing for facilitating the mixing operation.

7. Cartridge means as set forth in claim 1 wherein means is provided on the sealing means for engagement with a power source for transmitting rotation to the mixing means during a mixing operation.

8. Cartridge means as set forth in claim 1 wherein the sealing means comprises a stem member slidably secured to one of said housing sections, an outwardly extending circumferential flange provided on the stem for engagement with the inner periphery of said one housing section in one position of the sealing means and out of engagement with the sectional housing in a second position of the sealing means.

9. Cartridge means as set forth in claim 8 wherein the stem member is provided with a centrally disposed bore for engagement with a power source for shifting of the sealing means longitudinally within the sectional housing from said first to said second position and for transmitting rotation thereto for rotation of the mixing means.

* * * * *